United States Patent [19]

Clayton

[11] 4,117,847
[45] Oct. 3, 1978

[54] COLON CATHETER

[76] Inventor: Ralph S. Clayton, 3044 Fillmore Ave., El Paso, Tex. 79930

[21] Appl. No.: 679,567

[22] Filed: Apr. 23, 1976

Related U.S. Application Data

[63] Continuation-in-part of Ser. No. 655,444, Feb. 5, 1976, abandoned, and a continuation-in-part of Ser. No. 618,471, Oct. 1, 1975, abandoned.

[51] Int. Cl.$^2$ .............................................. A61M 25/00
[52] U.S. Cl. ..................................... 128/348; 128/2 F; 128/246; 128/283
[58] Field of Search .................. 128/2 F, 3, 4, 98, 226, 128/227, 239–246, 275, 283, 295, 341, 343, 344, 348–351, 128; D83/12 A

[56] References Cited

U.S. PATENT DOCUMENTS

| | | | |
|---|---|---|---|
| 565,386 | 8/1896 | Meengs | 128/246 X |
| 766,069 | 7/1904 | Sourwine | 128/245 |
| 1,116,825 | 11/1914 | Kells | 128/240 |
| 1,245,325 | 11/1917 | Dunn | 128/246 |
| 2,638,898 | 5/1953 | Perry | 128/283 |
| 2,713,340 | 7/1955 | Meminger | 128/98 |
| 2,873,739 | 2/1959 | Whann | 128/227 |
| 2,907,326 | 10/1959 | Gerarde | 128/216 |
| 2,923,296 | 2/1960 | Adams et al. | 128/227 |
| 3,132,645 | 5/1964 | Gasper | 128/3 |
| 3,459,175 | 8/1969 | Miller | 128/246 X |
| 3,548,828 | 12/1970 | Vasile | 128/283 |
| 3,641,999 | 2/1972 | Greene | 128/2 F X |
| 3,707,146 | 12/1972 | Cook et al. | 128/246 X |
| 3,765,401 | 10/1973 | Vass | 128/348 X |
| 3,771,522 | 11/1973 | Waysilk et al. | 128/240 X |
| 3,802,418 | 4/1974 | Clayton | 128/2 F |
| 3,826,242 | 7/1974 | Eggers | 128/341 |
| 3,938,521 | 2/1976 | Ritota et al. | 128/283 |

FOREIGN PATENT DOCUMENTS

5,445 of 1891 United Kingdom ................... 128/343

*Primary Examiner*—Dalton L. Truluck
*Attorney, Agent, or Firm*—Larson, Taylor and Hinds

[57] ABSTRACT

Improvements in a colon catheter for removing waste colon material, said catheter of the type having a hollow main tube insertable into the anal opening and held therein by an inflatable member located within the anal opening and limiting elements located outside of the anal opening and extending fore and aft from the main tube. The limiting elements may be formed as flat straps extending fore and aft from the main tube. The lower end of the catheter may be flared outwardly to form a widened exterior which forms the limiting elements and/or a widened lower interior. An irrigation tube or the like may be provided for directing enema fluid into the rectum above the inserted catheter. Obturator devices may be designed especially for use with the catheter including structure thereon to limit insertion and/or to secure the obturator in place. The obturator may also include a passage therethrough for administering enema fluid, in which the means for securing the obturator in place would resist expulsion of the obturator by the pressures built up in the anal canal by the injected enema fluid. A body strap retention device may be provided for securing the catheter in place, which strap retention device can be formed as an extension of the limiting elements. A collecton bag is formed integrally with or removably connected to the lower end of the catheter to collect waste material. This bag may be attached to the catheter with an obturator and/or enema fluid therein (or with means for inserting enema fluid therein) for cooperation with either or both of these elements for insertion of the obturator and/or injection of enema fluid. Alternatively, the bag and obturator may be separate and can be changed when the bag is full.

53 Claims, 21 Drawing Figures

COLON CATHETER

RELATED APPLICATION

This application is a continuation-in-part of pending U.S. Applications Ser. Nos. 655,444, filed Feb. 5, 1976, and Ser. No. 618,471, filed Oct. 1, 1975, both now abandoned.

BACKGOUND OF THE INVENTION

This invention relates to a medical device, and in particular it relates to improvements in a colon catheter of the type for removing waste colon material through the anal canal.

Until recently, procedures for cleaning the colon passage were the same as they had been for literally hundreds of years. These included the use of laxatives to stimulate explusion of solids, liquids or gases, enemas and/or stool softeners to soften and stimulate expulsive activity by the colon and finally, maneuvering the patient over an open receptacle such as a bedpan to collect materials expelled from the anal opening. These procedures are to say the least very inconvenient, even for healthy persons. But for those not in a healthy state, there are more serious medical and sanitary difficulties.

By all existing methods, the patient is not connected to the receptacle, permitting spillage, contamination, noise, and stench of feces and gases to escape.

For various reasons, a patient often cannot hold the anal canal open. This is a not infrequent occurrence following surgery but it also occurs at various other times, particularly with old persons, children and unconscious persons. However, even healthy persons can involuntarily fight releasing the colon contents. Another problem is that some patients, while able to hold the anal canal open, are not capable of remaining in one position for a long enough period of time to expel the colon contents such as is the case, for example, when using a bedpan or toilet. There are also serious sanitary and cleanliness disadvantages to the conventional bedpan. In addition to all of the above, it is often necessary for diagnostic purposes to observe the stool of the patient, and to collect all expelled feces, and this is often inconvenient or impossible when following presently known techniques for expelling the colon contents.

These and other disadvantages were solved, at least in part, by the invention disclosed and claimed in my previous U.S. Pat. No. 3,802,418, issued Apr. 9, 1974, in the specification of which patent the above described disadvantages existing in the prior art theretofore are discussed in greater detail.

The colon catheter as described in my said earlier patent constitutes a significant step forward in the art in that it provided for the first time a device insertable into the colon and maintainable therein for removing the colon contents. As such, it constituted a major step forward in the art in overcoming the various disadvantages which had existed theretofore.

However, notwithstanding the fact that my prior colon catheter constitutes a major step forward in the art, certain problems have been found to exist. Firstly, the cost of manufacturing a colon catheter as described in my said patent tended to be relatively high. Hence, there existed a need for simplifying the construction thereof. In addition, I have found that at times it is necessary or desirable to inject enema fluid into the space above the colon catheter while the latter is in place in the patient. In addition, I have found a need for providing new and varied arrangements and procedures for introducing enema fluid into the patient through the main tube after the device has been placed into the patient but before its actual use by the patient. Finally, I have found that in some patients the involuntary or voluntary reaction to the presence of the colon catheter in their bodies is to expel the entire colon catheter, expandable member and all, so that in these cases it is necessary to provide a further means for securing the colon catheter in place within the patient.

SUMMARY OF THE INVENTION

It is a purpose of the present invention to provide improvements for a colon catheter which solve the problems which have been found to exist with respect to my previous colon catheter as disclosed in my said earlier patent.

In accordance with a first aspect of the invention, there is provided an improved and highly simplified colon catheter wherein immediately beneath the part which passes up into the anal opening, the catheter is flared out in at least the forward and rearward direction if not also sideways. Such an arrangement significantly simplifies the overall design and construction of the catheter. The lower flared out portion not only provides a widened interior at the lower part for removing waste colon material, but it also provides the structure forwardly are rearwardly for constituting the "limiting elements" which cooperate with the expandable member to seal the anal opening.

In accordance with another feature of the present invention, an "irrigation tube" is provided in such a manner as to deliver enema fluid to the rectum above the colon catheter, and in particular, above the expandable member thereof, when the colon catheter is in place within the patient. The irrigation tube can be mounted to the exterior of the colon catheter such that the tube passes around the exterior of the expandable member or it can also be formed integrally within the wall of the colon catheter. In the former case, the tube can be of a sufficiently flexible material that it will be closed by the pressure exerted by the expandable member against the wall of the anal canal.

In still another feature of the present invention a colon catheter is provided which may be utilized in combination with various obturators, collection bag structures and enema fluid introducing means. For example, in accordance with one arrangement, a plastic collection bag is attached to the lower end of the colon catheter prior to insertion thereof in the patient. Since the colon catheter will probably be used once and disposed of, the collection bag may be permanently sealed directly to the catheter. The bag may actually contain the body of enema fluid placed therein, for example through a closable opening therein just prior to use, and/or an obturator. For convenience, the term "distal end" of the obturator will refer to the end which is inserted first into the catheter tube. The obturator may conveniently be double ended, i.e. constructed such that either end is capable of being a distal end inserted up into the catheter to serve as the obturator. The obturator would further include a raised part or the like positioned to engage the structure of the catheter for limiting insertion of the obturator up through the hollow main tube of the catheter and possibly also for securing the obturator in a fixed position therein. When injecting enema fluid into a patient, a pressure can build up in the anal canal up to approximately 5 psi. Hence, when injecting an enema fluid through the obturator, a means should be provided for securing the obturator in place against the fluid force in the anal canal tending to expel the same, until such time as it is desired to remove the obturator. By supplying the enema fluid directly within the plastic bag, in combination with the double ended obturator, the nurse or other medical attendant can then simply feel for the obturator and insert either end through the catheter for insertion into the patient and then remove the obturator and leave it loose in the bag and then simply manipulate the bag by rolling it or the like to cause the enema fluid to move up into the patient. Alternatively, the bag can be provided with a bar at the bottom thereof, wherein the bag can then be rolled up on the bar, forcing enema fluid to move into the patient. In addition, in either case the obturator can be hollow so that instead of removing it, the enema fluid can be injected directly therethrough while it is still in place in the catheter. Whenever using a hollow obturator, the opening at the upper end of the obturator may be positioned at the tip of, or on the side of the obturator but in any case located and constructed so as not to detract from the use of that said end as an obturator to ease insertion of the catheter into the patient.

In accordance with still another arrangement, an obturator of the type having a hollow passage therethrough can be connected to a suitable fluid line for introducing enema fluid therein. In the operation of this arrangement, the obturator can then be clamped and separated from the fluid line and the plastic bag connected to the lower end of the catheter before removing the obturator (in which case the obturator would then simply be lowered into the bag for disposal therewith).

In still another arrangement, the hollow obturator can be physically attached to the interior of the bag either directly or by means of a fluid line passing through the wall of the bag, and into and through the hollow obturator, whereby the enema fluid can be injected directly therethrough from an exterior supply source directly into the patient.

In accordance with still another feature of the present invention, means are provided for attaching the catheter directly to a patient's body as to the waist or the like by means of a suitable strap retention means or the like so as to prevent expulsion of the colon catheter from the patient as has happened in some instances.

In accordance with still another feature of the invention, it has been found quite advantageous to construct the limiting elements of a flat, strap-like material attached to the catheter tube and extending forwardly and rearwardly therefrom. These straps may form the straps of a strap retention means. This construction is simplified and hence economically advantageous.

Thus, it is a purpose of the present invention to provide a new improved colon catheter which solves problems which have been found to exist in my previous colon catheter.

It is a further object of this invention to provide new and improved colon catheter arrangements which are simplified and hence economically advantageous relative to the previous constructions.

It is another object of this invention to provide an improved colon catheter which comprises a lower portion which is flared out at least forwardly and rearwardly.

It is another object of this invention to provide an irrigation means for supplying enema fluid to the space above the catheter after it is in place in the patient and after the obturator means has been removed.

It is another object of this invention to provide improved obturator means for inserting the colon catheter into the anal opening.

It is still another object of this invention to provide improved enema fluid injection means for use in combination with the colon catheter of the present invention, either directly through an open catheter tube or through a hollow obturator located therein.

It is still another object of this invention to provide a collection bag constructed and arranged to cooperate with the catheter tube and/or with the obturator, to facilitate injection of enema fluid into the patient.

It is still another object of this invention to provide an improved colon catheter system comprising a plastic bag attached to the lower end of a colon catheter and including therein both enema fluid and a double ended obturator, the overall arrangement thus being essentially self-contained in that it includes therein, in addition to the catheter, the means for inserting the catheter, the means for injecting the enema fluid and the means for collecting the waste colon material.

It is still another object of the present invention to provide, in combination with a colon catheter, an obturator which serves the dual function of facilitating insertion of the colon catheter into the patient and also providing a passageway for the injection of enema fluid therethrough.

It is still another object of this invention to provide an improved colon catheter system including a collection bag attached to the lower end of the catheter and an obturator therein having a fluid passageway extending through the wall of the bag for receiving enema fluid from an external source and delivering the same directly into the patient.

It is still another object of this invention to provide a strap retention means for more positively securing the colon catheter to the body of the patient so as to positively prevent voluntary or involuntary expulsion of an inserted catheter.

It is still another object of the invention to provide a highly simplified strap retention arrangement wherein the limiting elements are formed as straps and extend to form straps of the strap retention means.

Other objects and advantages of the present invention will become apparent from the detailed description to follow, together with the accompanying drawings.

BRIEF DESCRIPTION OF THE DRAWINGS

There follows a detailed description of preferred embodiments of the invention to be read together with the accompanying drawings wherein.

DETAILED DESCRIPTION OF THE PREFERRED EMBODIMENTS

Referring now to the drawings, like elements are represented by like numerals throughout the several views.

My said prior U.S. Pat. No. 3,802,418 is incorporated by reference herein for its detailed discussion of the specifications of the colon catheter including various dimensions and selections of suitable materials. In addition thereto, it has since been appreciated that the catheter could be formed of many different materials including for example polyvinylchloride or clear polyethylene, the latter having the advantage that the attendant could visually identify any obstruction within the catheter. My said patent mentions that an optimum inside diameter might be on the order of 15 mm but no less than 10 mm. Further experimentation indicates that an optimum internal diameter might even be slightly greater, i.e. about 16 mm with an outside diameter of about 20 to 22 mm; but in any event, the exact internal diameter is not critical and can be varied over the range as indicated in my said patent.

Figure 1:
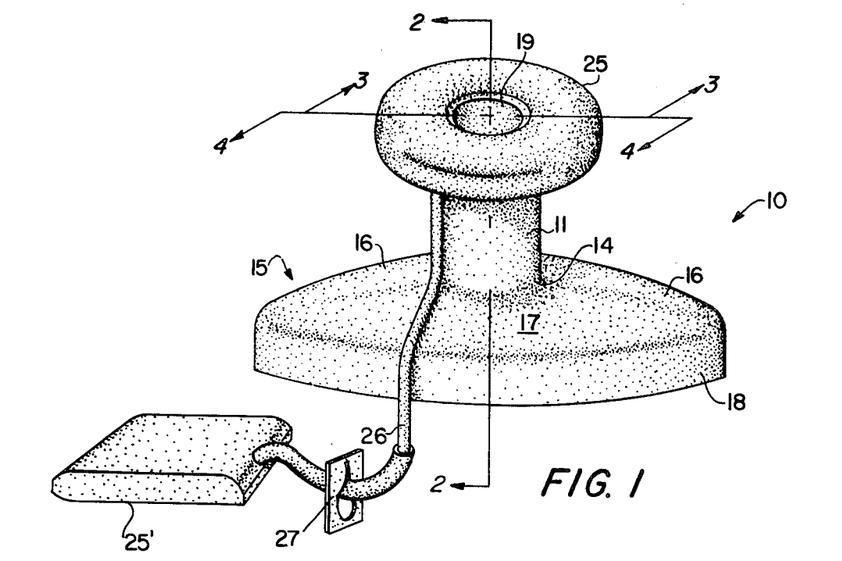
FIG. 1 is a perspective view of a colon catheter constructed in accordance with certain improved features of the present invention.
Figures 2, 3, 5:
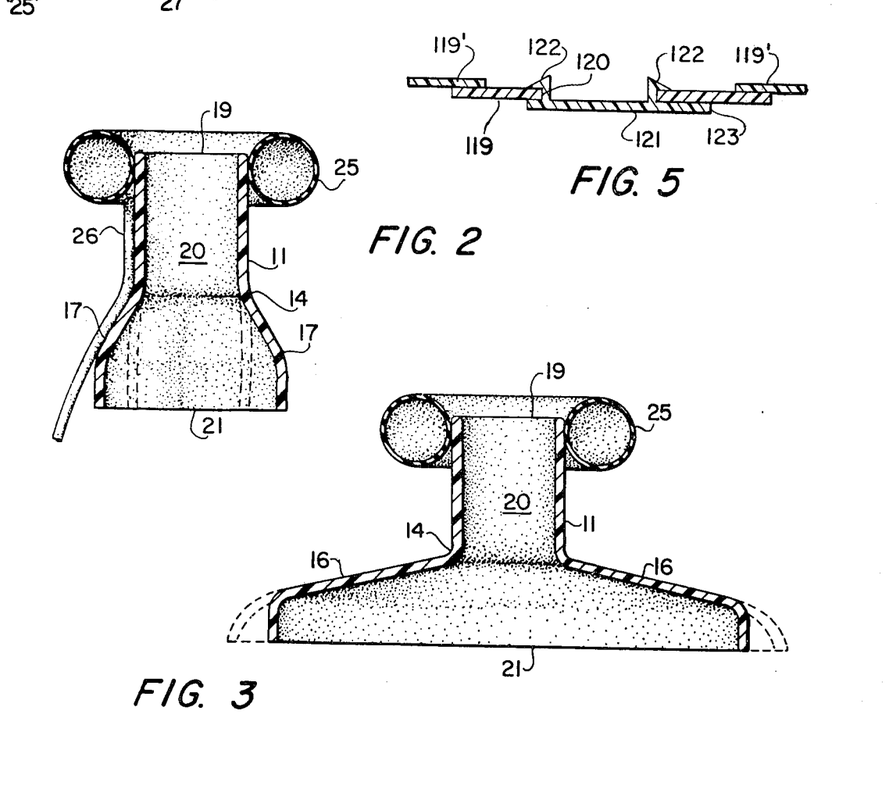
FIG. 2 is a vertical transverse cross-sectional view taken through the plane represented by the line 2—2 of FIG. 1.
FIG. 3 is a vertical longitudinal cross-sectional view taken through a plane represented by the line 3—3 of FIG. 1.
FIG. 5 is a partial cross-sectional view on an enlarged scale taken along line 5—5 of FIG. 4.

Referring now to FIGS. 1 through 3, there is shown an improved colon catheter 10 having an upper tube part 11, to the upper end of which is attached the torus shaped expandable balloon member 25. While the balloon is preferably circular in cross-section, as shown in FIGS. 2 and 3, it need not be exactly circular but may be otherwise such as oval, et cetera. Although the balloon member 25 may be formed out of almost any thin airtight material, one possibility is to make it out of a flexible non-stretchable material such as a vinyl fabric or the like since this will fix with certainty the size of the balloon member 25 in its expanded state. Alternatively, the balloon member 25 may be formed of a conventional expandible material such as latex, in which case control over the size of the expanded balloon could be controlled by other means, for example, by using a "safety cuff" 25' which is a member filled with a preselected volume of air and then connected to tube 26 so that one squeeze of 25' will transfer said predetermined quantity of air to member 25, after which line 26 would be closed by suitable means such as slot clamp 27. In either case, air under pressure is delivered to the member 25 through the tube 26 after member 25 has been located within the patient. The member 25 is preferably placed at the inner end of the anal canal at the terminal end of the rectum portion of the colon so that the open end of the catheter is positioned to receive fecal material located in the rectum. In the present description and in my previous patent the upper portion of the catheter is described as being circular. However, it will be understood that the invention is operable even if the catheter deviates from a circle such as oval, oblong, etc., so long as it will fit smoothly and comfortably through the anal opening. Such acceptable shapes will sometimes be referred to herein as "rounded."

In accordance with a first improved embodiment of the present invention, at the lower end of the upper part 11, the colon catheter turns outwardly at shoulder 14 to form the flared out lower tube part 15. The front and back portions 16 of this flared out part extend much farther then do the transversely extending portions 17. The reason for this is that the forwardly and rearwardly extending flared out portions 16 constitute in this embodiment the limiting elements which lie against the perineum for cooperating with the expandable member 25 for sealing the walls of the anal canal therebetween. The outer periphery of the flared out portions may include a downwardly extending skirt 18.

Referring to FIGS. 2 and 3, there is illustrated the upper opening 19 which in use would be located within the patient's rectum, an opening 20 extending through the catheter, which opening would have the said internal diameter of between 10 and 15mm inside the upper portion 11, and a widened lower opening 21.

As will be more evident from FIGS. 2 and 3, this improved colon catheter is highly simplified relative to the previous colon catheter in that it is of a far more simplified construction wherein it may be of essentially uniform wall thickness from top to bottom but concurrently include in its construction as an integral portion thereof means (the forwardly and rearwardly flared out portions) constituting the limiting elements for cooperating with the expandable member 25.

Actually, in practice it might be desirable to flare out the lower portion only in the front and back and not on the sides. The reason for this is that any sideways flare tends to interfere with the patient's upper thigh adjacent the anal opening so that discomfort results, especially in heavier persons. However, it has been found that at least some sideways flare 17 is necessary to prevent closing of the lower opening 21 when the patient's thighs exert lateral forces on the catheter tending to move the sides together. In FIGS. 2 and 3 dotted lines have been added showing the position of the flared out portions when subjected to such lateral forces as would be exerted thereon by a typical patient. Note that the lower part 15 will become elongated by extending forwardly and rearwardly (FIG. 3) while becoming more narrow transversely (FIG. 2).

Figure 4:
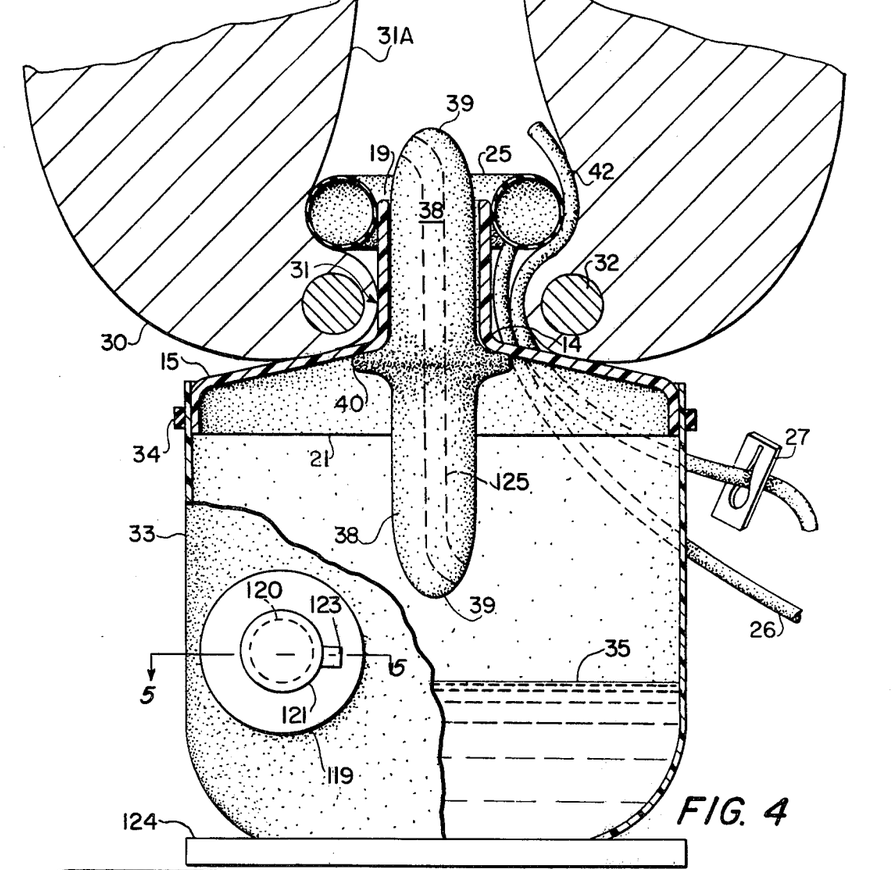
FIG. 4 is a longitudinal cross-sectional view taken through the colon catheter of FIG. 1 in the plane and in the direction as represented by the line 4—4 of FIG. 1 but showing the catheter in place within a patient and illustrating in addition certain modifications of the present invention.

FIG. 4 illustrates both (a) the colon catheter of FIGS. 1 through 3 in place within a patient and (b) a number of specific further improvements. Considering FIG. 4 first of all as a showing of the embodiment of FIGS. 1 through 3 within a patient, the patient, or more specifically the patient's pelvic floor is shown at 30. The colon catheter is shown inserted into the anal canal 31 passing the anal sphincter muscles 32 which control the opening and closing of the anal opening, and with the upper end thereof at the lower end of the rectum 31A. As shown in this figure, and as described in my said previous patent, when the colon catheter is in place within the anal canal, the anal canal itself is sealed between the upper tube part 11 on the inside, the expandable member 25 above, the limiting elements in the form of the flared out part 15 below, the elements 25 and 15 being spaced apart a small enough distance such that they exert vertical forces on the tissues in the vicinity of the anal canal in order to clamp the catheter in place and seal the anal opening so that any waste colon material must pass into the upper opening 19 and through the opening 20 of the catheter and past the lower opening 21.

The basic procedures for inserting any improved colon catheter has already been explained in considerable detail in my said previous patent. These procedures will therefore be repeated herein only in conjunction with the improvements described herein.

Turning again to FIG. 4, this time for its illustration of other specific improvements, the figure illustrates the following several improvements, and it will be understood that each of these improvements are essentially independent improvements and although they are illustrated in a single figure for purposes of convenience, each can be used with any of the others or independently of the others. Also, while they are shown with respect to the catheter embodiment of FIGS. 1-3, it will be apparent that they are equally adaptable for use with other embodiments of my catheter such as some of those shown in my said previous patent and the other embodiments shown and described in the present application.

Figures 6, 9, 11:
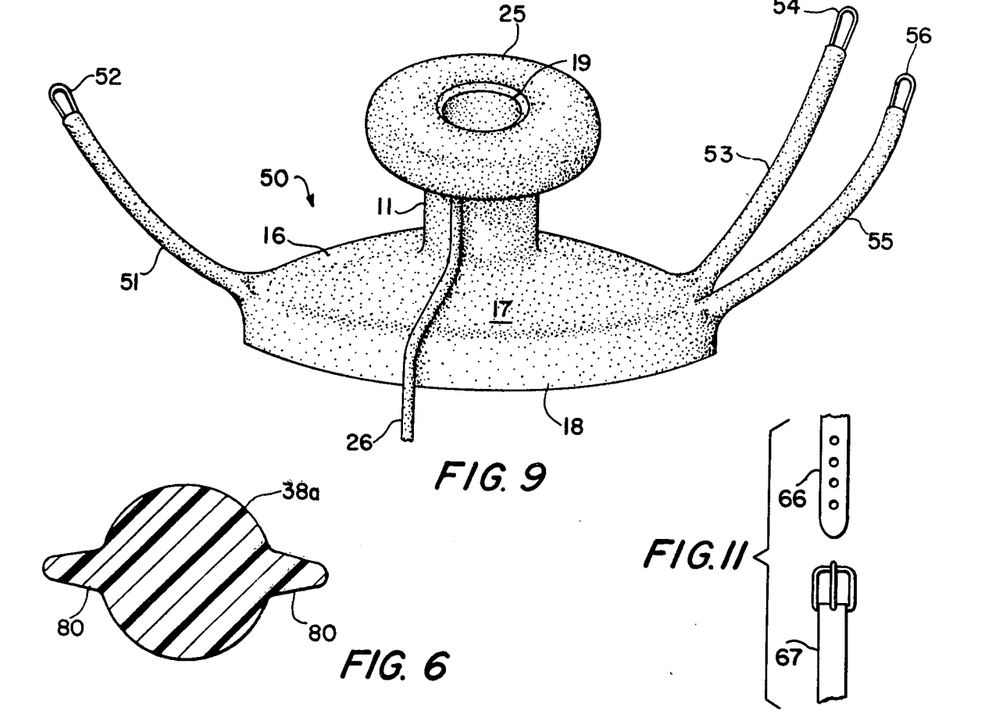
FIG. 6 is a horizontal central transverse cross-sectional view of a solid obturator similar to that shown in FIG. 4 but showing a modified version thereof.
FIG. 9 is a perspective view similar to FIG. 1 and showing an alternative embodiment of the present invention.
FIG. 11 illustrates a portion of FIG. 10, showing a modification thereof.
Figure 14:
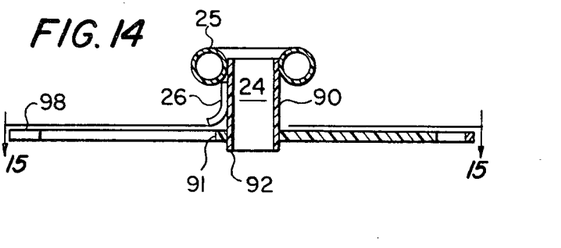
FIG. 14 is a longitudinal sectional view, taken in the plane 14—14 of FIG. 15, showing an alternative embodiment of a colon catheter.
Figure 15:
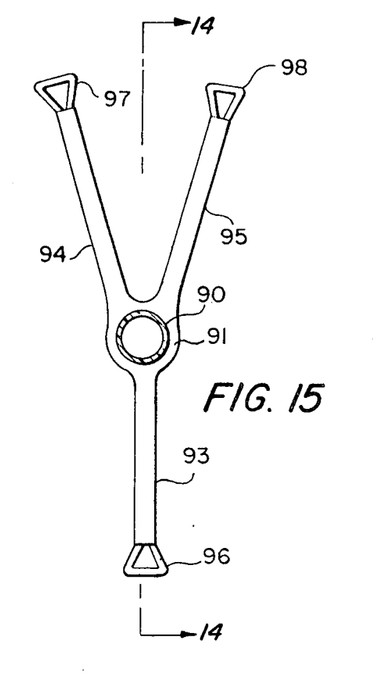
FIG. 15 is a horizontal cross-sectional view of the embodiment depicted in FIG. 14, taken along line 15—15 of FIG. 14.

Firstly, there is shown an improved obturator 38. It is of course understood that the purpose of an obturator is to assist in originally inserting the catheter into the patient. After this function, it has completed its usefulness is an obturator and it can either be stored for further use or disposed of. In the present case, the improved obturator is constructed such that either end can serve the obturating function. The ends 39 should be rounded and relatively soft to facilitate patient comfort while the shaft portions thereof should be relatively stiff so that the attendant can control movement of the catheter up into the patient. The improved catheter includes a circumferentially extending ridge 40 which cooperates with the internal surface of shoulder 14 so as to limit movement of the obturator up into the upper part 11 thereby controlling the exact depth of the obturator up into the upper part 11. When this type of obturator is used with a catheter tube which is cylindrical from end to end such as shown in FIGS. 1-3 of my previous patent or as shown in FIGS. 14 and 15 herein, the ridge 40 can simply be made to abut and hence cooperate with the lower end of the tube. A modified version of obturator 38 is shown in FIG. 6 at 38a which is identical to obturator 38 except that the circumferential ridge 40 is replaced by a pair of forwardly and rearwardly extending projections 80. This arrangement would be particularly suitable in the embodiment of FIGS. 1-3 in a situation wherein the laterally extending flared out parts 17 were held to a minimum, whereupon the projections 80 would simply abut the portions of shoulder 14 in the fore and aft plane for limiting the depth of insertion thereof.

A second improvement shown in FIG. 4 concerns the arrangement of the enema fluid. The colon catheter has attached thereto a conventional disposal collection bag 33 such as a plastic bag attached to the lower end of the catheter 10 by a suitable means such as elastic band 34. The bag may of course be attached by any suitable means or even permanently sealed to the catheter. A further improvement illustrated in FIG. 4 is the provision of the enema fluid 35 directly within this bag which will ultimately serve as the waste material collection bag. Although this constitutes a separate improvement, it is also highly useful in conjunction with the improved obturator 38. For example, in practice the catheter could be brought to the patient with the bag attached and with the enema fluid 35 and the obturator 38 therein. The attendant would then grasp the obturator through the wall of bag 33 and insert either end up into the catheter, insert the catheter, expand the member 25 so as to complete positioning of the catheter within the patient and then remove the obturator 38, letting it fall into the bag to be ultimately disposed of therewith, along with the waste material. In the meantime, as soon as the obturator has been removed, the attendant can cause the fluid 35 to be injected by rolling or otherwise compressing the bag 33. If desired, the neck of the bag can then be clamped to momentarily retain the enema fluid in the patient and then released to enter the bag.

Also shown in FIG. 4, as well as FIG. 5 is a means for introducing the enema fluid directly into the bag 33 through the wall thereof. For this purpose, bag 33 is provided with a thickened portion 119 formed as part of bag 33 or, as shown therein, formed as a separate piece and attached to bag 33 at 119'. In either case, portion 119 has an aperture 120 therethrough. Aperture 120 is covered with a resealable aperture means 121. Means 121 can, for example, comprise a snap lock mechanism 122 (FIG. 5) that is forced through aperature 120 and then snapped over the inside of the portion 119, locking aperture means 121 to aperture 120. A pull tab 123 is provided on means 121. Alternatively, resealable aperture means 121 can include an adhesive layer (not shown) for sealing means 121 to the outer wall surface of portion 119 of bag 33 about aperture 120. Enema fluid may be introduced into bag 33 through aperture 120 and then bag 33 can be rolled up so as to force fluid into anal opening 31. To facilitate such rolling up, a bar 124 can be fixedly attached to bag 33 so that bag 33 can be rolled up thereon. Another advantage of aperture 120 is that it can be opened to collect samples of stool therethrough for further examination while the catheter is still in place in the patient. Finally, as depicted in FIG. 4, obturator 38 can include a hollow central portion 125. Thus it is possible to insert obturator 38 into the colon catheter and force enema fluid through obturator 38 by rolling bag 33, with enema fluid therein, around bar 124.

A further improvement illustrated in FIG. 4 is the enema irrigation tube 42. The purpose of this tube is to inject enema fluid into the rectum above the expandable member 25 after the catheter is in place and in use within a patient. For example in some cases waste material in the rectum adjacent opening 19 can become so hard, i.e. "impacted" and/or large (the rectum 31A can typically expand up to about 5 inches while The anal opening 31 can typically expand 1 to 2 inches) that a patient who is in need of a colon catheter to hold open the anal canal cannot develop a sufficient force to "extrude" the hard and/or large mass of fecal material into opening 19. The tube 42 would serve the function of directing a small quantity of enema fluid up to this blocking fecal material to break the blockage and facilitate removal thereof. In addition, it would be most helpful to inject additional enema fluid when the patient is finished to be sure that the catheter tube is empty before removing it. The irrigation tube 42 would preferably be constructed of a relatively thin and "floppy" material so that when not in use, it would be pressed closed between the member 25 and the wall of the anal canal 31 so that waste material or fluid would not leak therethrough or thereby. The tube might be made, for example, of a thin walled material and have an internal diameter of 5 mm. Also shown in FIG. 4 is a suitable clamp 27 for the tube 42.

Figure 4A:
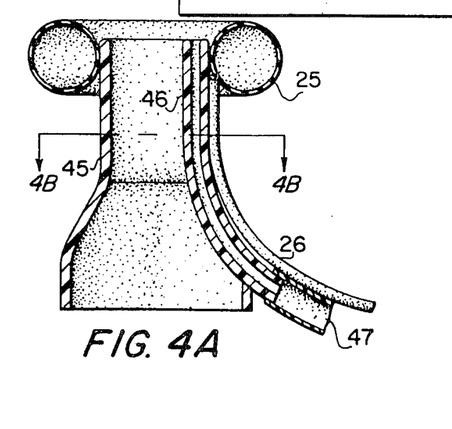
FIG. 4A is a cross-sectional view similar to FIG. 2 but showing a further modification of the invention.
Figure 4B:
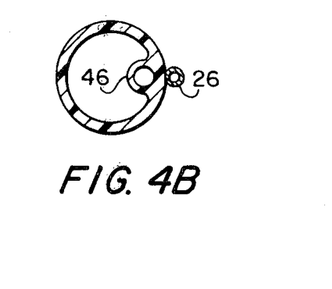
FIG. 4B is a horizontal cross-sectional view taken along line 4B—4B of FIG. 4A.

FIGS. 4A and 4B illustrate a modification of one feature of FIG. 4. In FIGS. 4A and 4B, a modified catheter 45 which is identical to the catheter 10 but for the modification, might include in place of the separate tube 42 a tube 46 formed integrally in the wall of the catheter 45. A suitable external tube 47 would be connected thereto, to which tube 47 a suitable clamp would be attached.

Figure 7:
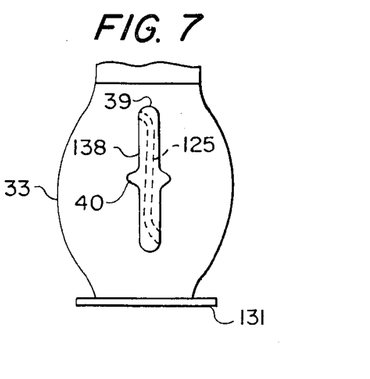
FIG. 7 is a partial side elevational view of a colon catheter, showing a further modification of the present invention.
Figure 8:
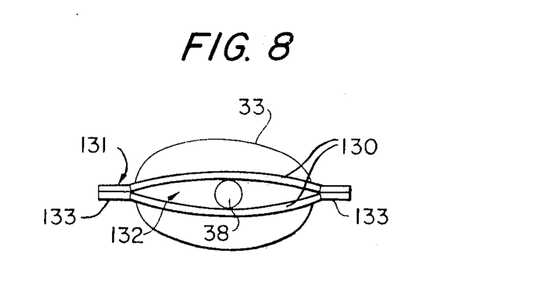
FIG. 8 is a bottom plan view of FIG. 7, showing the parts moved to a bag-opened position.

Turning to FIGS. 7 and 8, an additional modification of colon catheter 10 is depicted. This modification also provides for the introduction of enema fluid into bag 33 and eventually through the anal opening. Flexible bar 131 is comprised of a pair of flexible elements 130 which separate as shown in FIG. 8 to form an opening 132 through which enema fluid may be introduced into bag 33. The elements 130 of bar 131 then come together and fold over like the tope of a cookie package, to form the closed lower part of bag 33. The bag may then be rolled up about bar 131 in the same manner as on bar 124. Thereafter, the "ear" portions 133 of bar 131 extending out beyond the bottom of bag 33 can be bent in over the portion of bar 131 beneath bag 33 which have been rolled up about bar 131. This will prevent bag 33 from unrolling and will securely close aperture 130.

Figure 10:
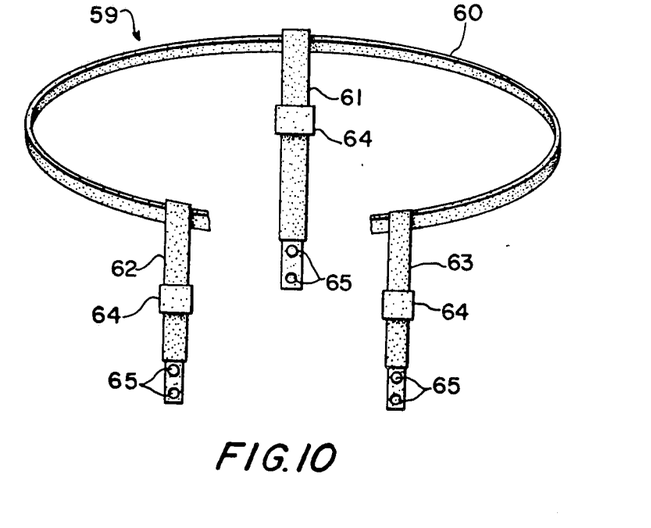
FIG. 10 illustrates a waist engaging strap retention adaptable for use by the patient in combination with the embodiment of the colon catheter shown in FIG. 9.

FIGS. 9 and 10 illustrate still another improvement of the colon catheter. As with the improvements of FIG. 4, it will be understood that the principle of this improvement can be used independently or in combination with any of the previously discussed improvements, i.e. with the catheter embodiment of FIGS. 1-3 or with other embodiments of the catheter. There is shown in FIGS. 9 and 10 a modified catheter 50 having a strap retention means for securing the catheter to the patient's body. It has been found that in certain instances, the rectum, being incapable of distinquishing the expandable member 24 from a fecal mass, might on occasion proceed to expel the entire catheter from the anal opening. The retention means, by attaching the entire catheter to the patient's body, will prevent this from happening. Referring now to FIGS. 9 and 10, the modified catheter 50 includes a posterior arm 51 having a suitable connecting means such as a rigid loop 52 at the end thereof, and a pair of forwardly extending arms 53 and 55, each having suitable connecting means such as rigid loops 54 and 56 formed at the ends thereof.

FIG. 10 illustrates a suitable retainer 59 for use in securing the catheter 50 in place. It includes a waistband 60 of webbing or heavy tape which is in the form of a conventional belt, the front of which including the belt buckle is broken away and omitted for purposes of clarity. A posterior strap 61 is provided on the waistband 60 and includes a vertical adjustment means 64 such as a conventional set of buckles or hooks, and includes a snap at the lower end thereof, the male and female members of which snap are shown as circle 65. The loop 52 would simply be placed between the two circles 65, whereupon the end of this strap 61 would be placed through the loop 52 and snapped for holding the posterior arm 21 in place. Similar straps 62 and 63 are provided for loops 56 and 54, respectively, for securing arms 55 and 53, respectively, these straps further including adjustment means 64 and a snap 65. Obviously any suitable connecting means such as buttons, buckles, etc., can be used to connect the arms to the harness. One such suitable connecting means is shown in FIG. 11 wherein element 66 represents any one of the straps of the strap retention means and 67 represents any one of the arms of the catheter. As represented by FIG. 11, the straps may include a plurality of openings therein while the arm 67 includes a belt buckle such that the connection between elements 66 and 67 is the same as for a conventional belt buckle connection. In this arrangement, adjustability is provided by selecting the appropriate hole in the strap 66.

Figures 12, 13:
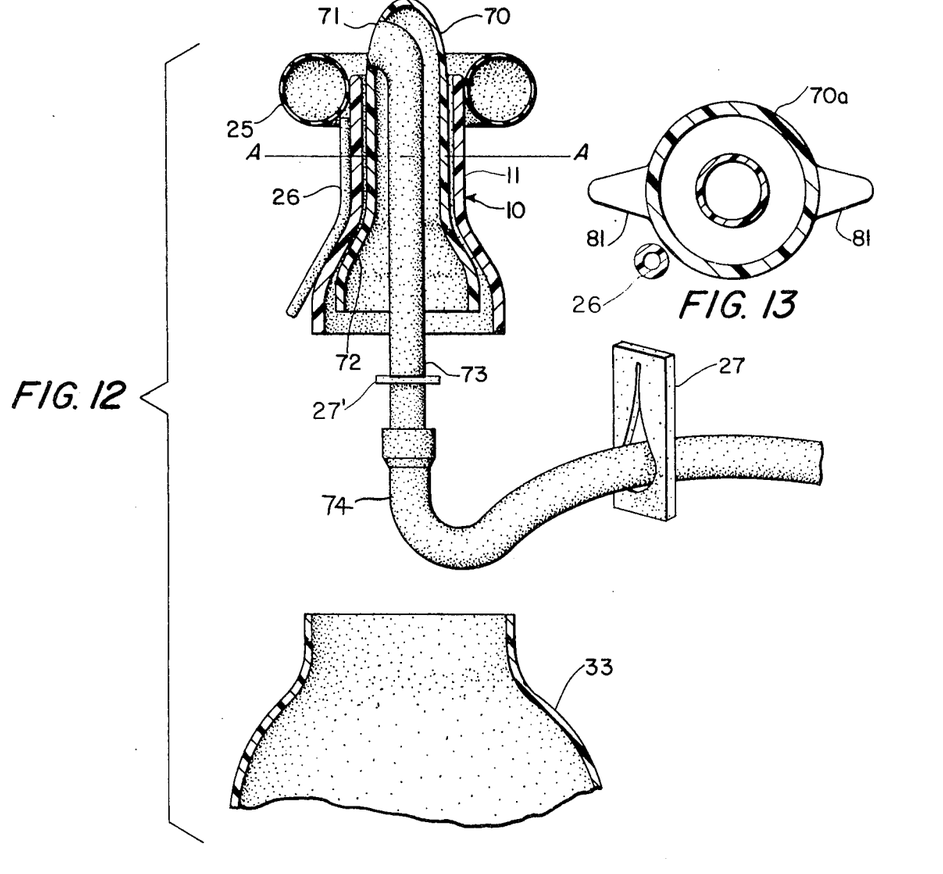
FIG. 12 is an exploded view showing a cross-sectional view of the main tube similar to FIG. 2, in combination with the elements of an obturating, enema fluid injecting and waste colon material collecting bag.
FIG. 13 is a cross-sectional view of a hollow obturator similar to that shown in FIG. 12, as if taken along a horizontal plane represented by line A—A thereof, but showing a modified version thereof.

A further improvement in colon catheters is shown in FIG. 12. Referring to this figure, there is shown the catheter 10 which is identical to that shown in FIG. 1. In addition, there is shown therein an improved obturator 70 which is of hollow construction. The distal end is rounded and smooth so as to facilitate insertion thereof as was the case with obturator 38 and a shoulder 72 is provided for limiting insertion of this obturator into the upper portion 11 of the catheter 10. In addition, this hollow obturator is provided with means including a tube 73 which opens on the side or end of the distal end of obturator 70 for introducing an enema fluid into the patient.

Utilizing the system of FIG. 12, an enema tube 74 having a clamp 27 thereon can then be attached to the lower end of tube 73 for inserting enema fluid. After this has been completed, a further clamp 27' on tube 74 can be closed, after which the bag 33 would be attached to the lower end of the catheter, whereupon the obturator could be grasped through the wall of bag 33, pulled out and allowed to fall into bag 33.

FIG. 13 illustrates a modified obturator 70a wherein the circumferentially extending shoulder 72 has been replaced by forwardly and rearwardly extending projections 82 provided for the same purpose as the projections 80 of FIG. 6, namely for use with a catheter having little or no laterally extending flared out portion 17.

FIGS. 14 and 15 illustrate another embodiment of a colon catheter made in accordance with the present invention, this embodiment including a cylindrical tube 90 which is similar to that shown in FIGS. 1-3 of my previous patent, together with an improved arrangement of limiting elements. The limiting elements of FIGS. 14 and 15 are particularly adapted for use with a harness means of the type as shown in FIG. 10. As with the improvements of FIG. 4, it will be understood that the present improvement can be used independently or in combination with any of the previously discussed improvements. It will also be understood that all of the various improvements concerning the obturators, collection bags, enema fluid injection arrangements, and the irrigation tube are usable with the basic colon catheter embodiment shown in FIGS. 14 and 15.

Referring to FIGS. 14 and 15, the limiting means comprises a generally flat member which includes a central portion 91 that is fixedly attached approximately 5 mm from lower end 92 of tube portion 90, and which includes a posterior arm 93 and anterior arms 95 and 95. In one preferred arrangement the front arms may extend about 18 cm and the rear arms about 16.5 cm. Firstly, these elements constitute simplified limiting elements which, like the previously described limiting elements, cooperate with the tube part 90 and the expandable member to seal off the anal opening. Secondly, these arms perform a function similar to arms 51, 53 and 55 as part of the harness means. Arms 93, 94 and 95 have loops 96, 97 and 98, respectively, fixedly attached thereto, loops 96, 97 and 98 positioned distally from the point of attachment of arms 93, 94 and 95 to portion 91. Loops 96, 97 and 98 are engaged by retainer 59 (FIG. 10) in the same manner that loops 52, 54 and 56 (FIG. 9) are engaged thereby. As with the embodiment of FIGS. 9 and 10, obviously other known connecting means such as the belt buckle arrangement of FIG. 11, buttons, etc. can be used to connect the arms to the retainer. This embodiment can be manufactured most economically. For example, the arms 93, 94 and 95 and portion 91 of th modified catheter can simply be die-cut from a piece of vinyl fabric, eliminating the need for more costly molding procedures.

Figure 16:
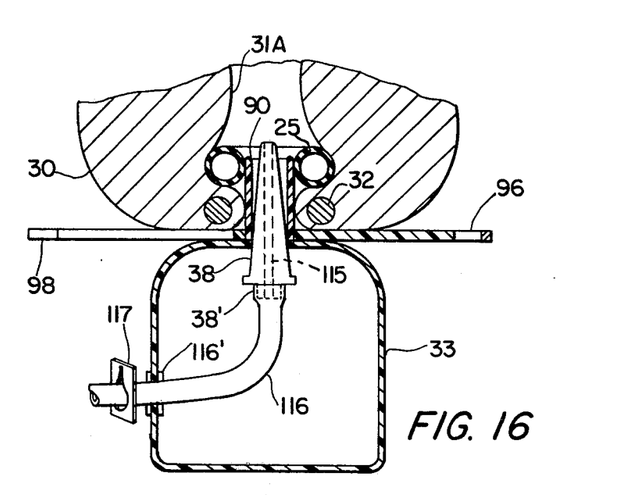
FIG. 16 is a longitudinal cross-sectional view taken through a colon catheter similar to that shown in FIGS. 14 and 15, in the plane and in the direction as represented by the line 14—14 of FIG. 15, but showing the catheter in place within a patient and illustrating in addition several modifications of the present invention.

FIG. 16, like FIG. 4 illustrates a plurality of difference improvements, each one of which is capable of being used independently of the others. Firstly, FIG. 16 illustrates a colon catheter similar to that shown in FIGS. 14 and 15 with an important difference that the strap type limiting means is given a smaller central aperture and is connected by suitable sealing means directly to the bottom rather than the lateral exterior of the tube 90. A second improvement illustrated in FIG. 16 is that the bag 33, if it is of the type to be permanently sealed with respect to the catheter, can conveniently be sealed to the bottom of the limiting means rather than to the tube of the catheter. This provides a somewhat greater horizontal area for sealing purposes.

Still another improvement of FIG. 16 is the concept of providing an obturator such as 38 with a fluid passage 115 in direct fluid communication with the exterior of bag 33 for the insertion of enema fluid directly therethrough. In FIG. 16 the obturator 38 is connected by a suitable connection 38' to tubing 116 which passes through the wall of bag 33 at a sealed opening 116'. In use distal end of the the obturator is inserted into the tube 90 as shown for insertion into the patient and enema fluid is delivered through tube 116 after which the tube is closed off by clamp 117. After the enema has been held in the patient a sufficient time, the operator simply grasps the oburator 38 or the tube 116 through the wall of bag 33 to remove the obturator to permit removal of waste colon material through the catheter into the bag.

Figure 17:
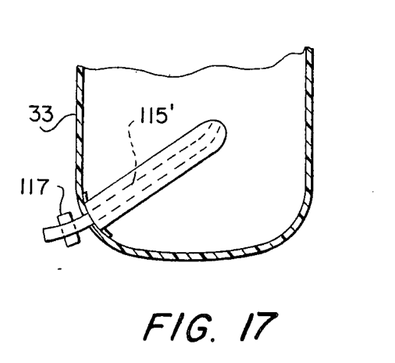
FIG. 17 is a partial cross-sectional view of a collection bag in combination with an obturator and showing a further modification of the invention.

As an alternative to the particular embodiment shown in FIG. 16 of the concept involving direct injection of fluid through the wall of the bag and into and through an obturator, reference in made to FIG. 17 which illustrates an alternative arrangement wherein the obturator, instead of being connected to the wall of the bag via a flexible tube 116, is connected directly thereto.

Another improvement illustrated in FIG. 16 is the provision of a tapered obturator. Although the diameter of the obturators described heretofore have had essentially the same diameter at their distal ends as the inside diameter of the catheter tube, it has been found operable as well as economically advantageous to use an obturator having a much smaller diameter at the upper end thereof. This will be operable and will not reduce patient comfort so long as the distal end of the obturator, although small, is rounded at its edges.

As is evident from the various embodiments discussed heretofore, the method for fixedly attaching the bag 33 to the colon catheter can vary considerably. The figures illustrate a permanent seal such as a heat seal and a clamp. Any other suitable means may be included such as a threaded connection, a snap lock, etc.

Figure 18:
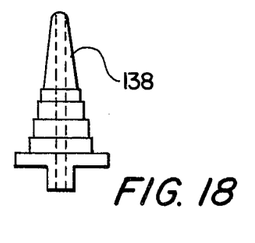
FIG. 18 is a side elevational view of a further obturator showing a modification of the invention.
Figure 19:
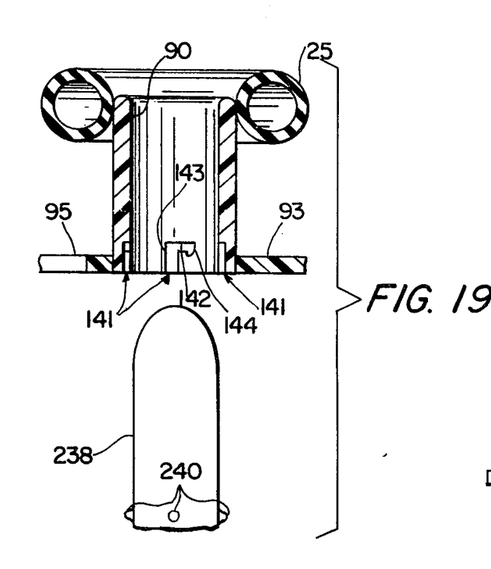
FIG. 19 is a partial longitudinal sectional view showing a colon catheter similar to that shown in FIGS. 14 and 15 in combination with an obturator and illustrating another modification of the present invention.

A further improvement of the present invention which is illustrated in FIG. 16 as well as FIGS. 18 and 19 relates to a means for removably securing the obturator within the catheter tube. Previously there was discussed the concept of providing a limiting means such as the shoulder 40 of FIG. 4 for limiting insertion of the obturator up into the catheter tube. However, on occasion it may be necessary to physically secure the obturator in place to prevent expulsion thereof. When enema fluid is injected into a patient, it is injected under a slight pressure which may create a pressure of up to 5 pounds per square inch in the rectum. After injection, it is necessary to hold the fluid within the rectum for a predetermined period of time to permit the enema fluid to act on the waste material therein. Hence, it means were not provided for securing the obturator in place during this waiting period, then the obturator might well be expelled involuntarily. On the other hand, the means for securing the obturator in place must be removable so as to permit the operator to remove the obturator at the appropriate time to permit removal of the waste colon material into the collection bag. In FIG. 16, this securing means is provided in the form of the tapered obturator 38. Specifically, the resilient nature of the plastic tube 90 is such that when the obturator 38 is urged up into the catheter tube 90, it will compress the bottom of tube 90 thereby forming a strong frictional engagement. It will be apparent that one skilled in the art, given these teachings, can select materials of a proper resiliency and with proper surface characteristics such that a frictional engagement is achieved which will withstand 5 p.s.i. in the rectum. At the appropriate time, the operator can then simply reach through the wall of bag 33 and grab either the obturator 38 or the tube 116 (assuming that the connection 38' is a strong one which it would normally be) and simply pull the obturator out of the catheter tube.

FIG. 18 illustrates a somewhat modified obturator 138 which is similar to oburator 38 except that it includes a plurality of steps rather than a uniformly tapered surface. It will be understood that these steps might provide a somewhat stronger frictional hold on the tube 90 since the engaging surfaces would be more closely parallel to the axis of the obturator 38. However, an obturator such as 138 would of course be slightly more expensive then the oburator 38 of FIG. 16.

FIG. 19 illustrates still another embodiment for removably securing an obturator in place. This figure illustrates a catheter tube similar to that of FIGS. 14 and 15 which has been modified to include "bayonet" type grooves 141 each comprising an inverted L-shaped channel having a vertical leg 143 communicating with a horizontal base 142 which terminates at an enlarged portion 144. In the illustrated embodiment, four such grooves are provided, each spaced 90° about the circumference of the interior of tube 90. Three of these are visable in FIG. 19. Obviously any number of such grooves can be provided. Also shown in FIG. 19 is an obturator 238 having pipes 240 extending outwardly therefrom, one for each of the grooves 141. In a manner which is well known with respect to bayonet type joints, the obturator is inserted up into the catheter tube 90 such that each of the pips 240 enter the open lower end of a respective channel 143 until the pips engage base 142 whereupon the obturator is turned clockwise (viewed from above) until the pips 240 drop into their respective enlargements 144. This type of connection can of course withstand much greater forces and removal is accomplished simply by reversing the insertion procedure.

Although the invention has been described above in considerable detail with respect to preferred embodiments thereof, it will be apparent that the invention is capable of numerous modifications and variations apparent to those skilled in the art without departing from the spirit and scope of the invention.

I claim:

1. A catheter for removing solid and other waste material from the colon through the anal opening comprising:

an elongated hollow tube of solid non-inflatable construction having means defining an upper opening at an upper end of the tube and means defining a lower opening at the lower end of the tube, and including a lumen of sufficient cross-section for the passage of solid waste-colon material from the upper opening therethrough to the lower opening, the upper part of the tube being rounded and being insertable into the anal opening, an annular expandable member fixed to and encircling the upper part adjacent the upper opening and constructed to be expanded radially outwardly to circumferentially surround the tube adjacent the said upper opening to seal off the anal canal such that waste material can escape from the colon only through the hollow tube, and including means for directing fluid to the expandable member to expand it after it is located within the anal canal, said catheter including a shoulder at the lower end of the upper part, at which shoulder the material of the tube flares outwardly to form a flared out part of essentially uniform thickness from said shoulder to the lower end of the flared out part which is at the lower end of the tube, such that the flared out part flares out essentially similarily both externally and internally, said exterior of the flared out part including surface means extending at least forwardly and rearwardly to lie against the perineum fore and aft of the anal opening to limit movement of the upper part up into the anal opening, the spacing along the exterior of the tube between the expandable member and the surface means being such that after the upper part of the tube has been inserted into the anal opening and the expandable member expanded, the anal canal is compressed vertically between the annular expandable member and the surface means to seal the anal canal externally of the tube such that waste colon material flows out only through the tube and including means at the lower end of the tube for securing a collection bag to the enlarged lower end of the flared out part for the passage of waste-colon material out of the enlarged lower end and into the collection bag.

2. A catheter according to claim 1, including a lower part of the tube extending downwardly from the outer periphery of the flared out part.

3. A catheter according to claim 1, said flared out part being flared out all around the circumference of the tube and extending forwardly and rearwardly a greater distance than it extends transversely to said fore and aft directions.

4. A catheter according to claim 1, including a collection bag attached by clamp means to the lower end of the tube, and including an obturator within the bag, said obturator being elongated and constructed such that either end fits through the tube, said obturator including ridge means positioned on the side of the obturator to engage the interior of the shoulder to limit movement of the obturator up into the tube.

5. A catheter according to claim 4, including an enema fluid in the bag.

6. A catheter according to claim 1, including a harness means for attaching the catheter to the patient's body at or above the waist to prevent removal of the catheter from the patient's anal opening.

7. In combination, a colon catheter for removing solid and other waste material from the colon through the anal opening and an obturator for facilitating insertion of the catheter into the anal opening, comprising, an elongated essentially cylindrical imperforate hollow tube having means defining an upper opening at the upper end of the tube and means defining a lower opening at the lower end of the tube and aligned with the upper opening, and including a lumen extending stright through the tube and having a diameter of at least 10mm from the upper opening thereof to the said aligned lower opening thereof for the passage of solid as well as other waste-colon material from the upper opening therethrough to the lower opening, the upper end of the tube being insertable into the anal opening, an annular expandable member fixed to and encircling the upper end adjacent the upper opening and constructed to be expanded circumferentially outwardly to surround the end of the tube at the said upper opening to seal off the anal canal such that waste material can escape from the colon only through the hollow tube, and including means for directing fluid to the expandable member to expand it after it is located within the anal canal, limiting means attached to the tube vertically spaced from the expandable member and extending outwardly at least forwardly and rearwardly thereof to limit movement of the upper end up into the anal opening, the spacing along the exterior of the tube between the expandable member and the limiting means being such that after the upper end of the tube has been inserted into the anal opening and the expandable member expanded, the anal canal is compressed vertically between the annular expandable member and the limiting means to seal the anal canal externally of the tube such that waste-colon material flows outwardly only through the tube, said obturator having a distal end which is essentially smooth and round, and said obturator being insertable into said lower opening until the distal end is located in the vicinity of the upper opening, and being completely removable through the lower opening to permit the flow of waste material therethrough, a passageway through the obturator for the delivery of fluid therethrough and including an opening in the vicinity of the distal end of the obturator positioned to permit fluid to flow out said opening and into the patient when the obturator is in place in the hollow tube, and engagement and sealing means on the said obturator and the said tube for engaging the obturator with only cooperating parts of the bottom or interior of the hollow tube to positively limit movement of the obturator into the hollow tube, to watertightly seal the obturator with the hollow tube to prevent the flow of liquid between the obturator and the hollow tube, and to prevent the expulsion of the obturator under the pressure exerted by the fluid introduced into the patient through the obturator while permitting intentional and complete removal of the obturator through the lower opening to permit the flow of waste material through the lower opening.

8. The combination according to claim 7, said obturator having at least some portions engaging the interior of the hollow tube along essentially the entire internal surface thereof except in the vicinity of the upper opening of the hollow tube.

9. A combination according to claim 7, said engagment and sealing means comprising a tight frictional fit between the obturator and the hollow tube at at least one point along the length of the obturator.

10. A combination according to claim 7, the distal end of the obturator being a rounded solid end with said opening located on the side of the obturator near said distal end.

11. A combination according to claim 7, said obturator being tapered from a reduced cross-section at the distal end to a larger cross-section which forms the watertight seal between the obturator and the hollow tube.

12. A combination according to claim 11, the distal end of the tapered obturator being rounded and solid, the said opening being located alng the side of the obturator.

13. A catheter according to claim 7, said elongated hollow tube having an interior including a widened portion at the lower end thereof forming an internal shoulder within the interior therof, said engagement and sealing means comprising a raised portion of said obturator engaging said internal shoulder in the colon catheter to limit movement of said obturator therethrough.

14. A catheter according to claim 13, said obturator including said raised portion located centrally along its length and including said rounded end and said cross-section which fits through the hollow tube at both ends of the obturator, whereby either end of the obturator is capable of being inserted through the hollow tube.

15. A catheter according to claim 14, including a disposable collection bag connected to the lower end of the hollow tube, said obturator being located in said bag prior to useage thereof.

16. A catheter according to claim 7, said engagement and sealing means comprising a raised ridge extending circumferentially all around the obturator.

17. A catheter according to claim 7, said engagement and sealing means comprising a raised portion comprising projections on only opposed sides of the obturator.

18. A catheter according to claim 7, said engagement and sealing means engaging the said lower end of the hollow tube to limit movement thereof into the catheter.

19. A catheter according to claim 7, including a disposable bag connected to the lower end of said catheter, said obturator being located in said bag.

20. A catheter according to claim 19, said bag further including an elongated bar fixedly attached to said bag at a location positioned opposite from the location of connection of said bag to said catheter, and wherein said bag is flexible so that it can be rolled up about said elongated bar, reducing the volume of said bag and forcing enema fluid into said hollow tube.

21. A catheter according to claim 20, including an opening formed in and closable by said elongated bar.

22. A catheter according to claim 19, said bag further including an aperture in the wall of the bag and a resealable closure means for allowing access to said bag through said aperture.

23. A catheter according to claim 22, wherein said resealable means includes a snap lock.

24. A catheter according to claim 7, including a disposable bag connected to the lower end of the catheter, said obturator including a fluid passageway therethrough, the end of the obturator opposite said distal end operatively connected to the bag such that the fluid passageway passes through the wall of the bag.

25. A catheter according to claim 24, including a flexible conduit connected to the said opposite end of the obturator and passing through the wall of the bag.

26. A catheter according to claim 24, the said opposite end of the obturator being fixed to the interior of the bag, and an opening in the bag placing the exterior of the bag into fluid communication with the said obturator passageway.

27. A catheter according to claim 7, wherein said engagement means further includes securing means for removably securing said obturator at a predetermined position along the interior of the hollow tube.

28. A catheter according to claim 27, wherein said engagement and sealing means comprised at least one raised pip of a twist lock on the obturator and at least one groove located at the lower end of said lumen of the hollow tube for receiving said pip, said obturator being slidable into said lumen and then twisted, lockingly positioning said pip in said groove of said twist lock.

29. A catheter according to claim 27, said securing means including a tapered outer shape of the obturator which tapers from a first width at the rounded end which is less than the interior width of the hollow tube to a portion having a width greater than the interior width of the hollow tube, whereby as the larger portion of the obturator enters the tube it resiliently compresses the same such that said resilient compression and the frictional engagement between the obturator and the hollow tube removably secure the obturator in place in the hollow tube.

30. A catheter according to claim 29, said obturator having a uniform taper.

31. A catheter according to claim 29, said obturator having a stepped taper.

32. A catheter for removing solid and other waste material from the colon through the anal opening comprising:

an elongated hollow tube having means defining an upper opening at the upper end of the tube and means defining a lower opening at the lower end of the tube, and including a lumen having a diameter of at least 10 mm from the upper opening thereof to the lower opening thereof for the passage of solid as well as other waste-colon material from the upper opening therethrough to the lower opening, the upper end of the tube being insertable into the anal opening, an annular expandable member fixed to and encircling the upper end adjacent the upper opening and constructed to be expanded circumferentially outwardly to surround the end of the tube at the said upper opening to seal off the anal canal such that waste material can escape from the colon only through the hollow tube, and including means for directing fluid to the expandable member to expand it after it is located within the anal canal, limiting means attached to the tube vertically spaced from the expandable member and extending outwardly at least forwardly and rearwardly thereof to limit movement of the upper end up into the anal opening, the spacing along the exterior of the tube between the expandable member and the limiting means being such that after the upper end of the tube has been inserted into the anal opening and the expandable member expanded, the anal canal is compressed vertically between the annular expandable member and the limiting means to seal the anal canal externally of the tube such that waste-colon material flows outwardly only through the tube, a strap retention means for attaching the catheter to the patient's body at or above the patient's waist to prevent expulsion of the catheter from the anal opening, said strap retention means including arm means connected to and extending forwardly and rearwardly from the limiting means to a body engaging means to prevent involuntary explusion of the catheter downwardly out of patient's anal opening during muscle movements of the patient attempting to expel waste-colon material, a collection bag connected to the lower end of the hollow tube for collecting waste-colon material passing through the lumen and out the lower opening thereof, the top of the collection bag located beneath the strap retention means and having an opening at least 10mm to provide a continuation of the unobstructed passageway of the hollow tube outwardly into the collection bag, and including an insert means insertable into the hollow tube for injection of liquid into the patient, and removable from the hollow tube to permit solid and liquid waste material to pass completely through the hollow tube and out the lower opening thereof and into the collection bag.

33. A catheter according to claim 32, said body engaging means mountable on the patient's body and including connections for removably connecting the body engaging means with the connecting arms.

34. A catheter according to claim 32, including two arms extending forwardly, one on each side of the center plane of the patient and one arm extending rearwardly.

35. A catheter according to claim 32, said connecting arms being formed integrally with the limiting means.

36. A catheter according to claim 35, said limiting means including a generally flat strap member having a central area with an aperture therethrough, said elongated hollow tube connected to said central area, said connecting arms fixedly attached to and extending from the outer circumferential edge of said central area.

37. A catheter according to claim 36, said elongated hollow tube extending 5mm below said strap member.

38. A catheter according to claim 36, said limiting means connected to the lower end of the hollow tube.

39. A catheter according to claim 32, said limiting means comprising:

a shoulder near the lower end of the hollow tube, at which shoulder the material of the hollow tube flares outwardly to form a flared out part, the exterior of which flared out part includes surface means extending at least forwardly and rearwardly to lie against the patient's body fore and aft of the anal opening, and said front and rear connecting arms being integral with and extending respectively forwardly and rearwardly from said flared out part.

40. A catheter according to claim 32, including a pair of forwardly extending connecting arms, one on each side of the center plane through the patient, and one posterior arm located on the patient's central plane.

41. A catheter according to claim 32, including an irrigation tube for directing enema fluid to the space above the upper end of the hollow tube after the hollow tube has been inserted into the anal opening.

42. A catheter according to claim 41, said irrigation tube means comprising a separate tube extending along and connected to the exterior of the hollow tube and across the exterior of the expandable member.

43. A catheter according to claim 42, said irrigation tube means being of sufficiently flexible material such that it is capable of collapsing between the expanded expandable member and the walls of the anal canal when enema fluid is not being forced therethrough, to thus prevent leakage of wast colon material outwardly therethrough.

44. A catheter according to claim 42, said separate tube extending between the said hollow tube and the expandable member.

45. A catheter according to claim 41, said irrigation tube means comprising a passageway formed integrally in the wall of the hollow tube.

46. A catheter for removing solid and other waste material from the colon through the anal opening comprising:

an elongated hollow tube having means defining an upper opening at the upper end of the tube and means defining a lower opening at the lower end of the tube, and including a lumen having a diameter of at least 10mm from the upper opening thereof to the lower opening thereof for the passage of solid as well as other waste-colon material from the upper opening therethrough to the lower opening, the upper end of the tube being insertable into the anal opening, an annular expandable member fixed to and encircling the upper end adjacent the upper opening and constructed to be expanded circumferentially outwardly to surround the end of the tube at the said upper opening to seal off the anal canal such that waste material can escape from the colon only through the hollow tube, and including means for directing fluid to the expandable member to expand it after it is located within the anal canal, limiting means attached to the tube vertically spaced from the expandable member and extending outwardly at least forwardly and rearwardly thereof to limit movement of the upper end up into the anal opening, the spacing along the exterior of the tube between the expandable member and the limiting means being such that after the upper end of the tube has been inserted into the anal opening the expandable member expanded, the anal canal is compressed vertically between the annular expandable member and the limiting means to seal the anal canal externally of the tube such that waste-colon material flows outwardly only through the tube, a strap retention means for attaching the catheter to the patient's body at or above the patient's waist to prevent expulsion of the catheter from the anal opening, said strap retention means including arm means connected to and extending forwardly and rearwardly from the limiting means to a body engaging means to prevent involuntary expulsion of the catheter downwardly out of patient's anal opening during muscle movements of the patient attempting to expel waste-colon material, said limiting means comprising a generally flat thin layer of plastic material permanently heat sealed to the lower end of the hollow tube and encircling the same, and said strap retention means including thin flat straps connected to said limiting means and extending forwardly and rearwardly therefrom.

47. A catheter according to claim 46, including a collection bag permanently heat sealed with respect to the limiting means and the hollow tube into a position beneath the limiting means and the straps such that the straps extend outwardly above the bag, and an uninterrupted path is provided through the hollow tube and into the collection bag.

48. A catheter according to claim 46, said straps including a pair of forwardly extending arms, one on each side of the center plane of the patient, and one rearwardly extending arm.

49. A catheter according to claim 48, said arms having connecting means at their ends remote from the hollow tube for connection to a waste retainer device.

50. In combination, a colon catheter for removing waste material from the colon through the anal opening and an obturator for facilitating insertion of the catheter into the anal opening, said catheter comprising:

an elongated hollow tube having means defining an upper opening at an upper end of the tube and means defining a lower opening at the lower end of the tube, and including a lumen of sufficient cross-section for the passage of solid waste-colon material from the upper opening therethrough to the lower opening, the upper part of the tube being rounded and being insertable into the anal opening, sealing means at the upper end of the upper part for sealing the upper end of the catheter in the anal opening and limiting means positioned at the lower end of the upper part for contacting the perineum fore and aft of the anal opening and for cooperating with the sealing means to seal the anal opening, and said obturator being elongated and having a smooth rounded distal end and having a cross-section adjacent said distal end which fits smoothly through the upper part of the hollow tube, said obturator including a raised portion along the length thereof positioned to engage a portion of the said colon catheter to limit movement of the obturator therethrough, and including a collection bag connected to the lower end of the hollow tube such that waste material passing through the lumen passes into the bag, said obturator including a fluid passageway therethrough, connecting means for operatively connecting the end of the obturator opposite said distal end to the bag such that the fluid passageway passes through the wall of the bag and the bag is sealed around the opening of said passageway through the bag such that it is water tight for collecting the waste-colon material, said fluid passageway which passes through the wall of the bag hence constituting means for delivering enema fluid from a location external of the bag through the passageway into the patient with the collection bag in place in the hollow tube.

51. The combination according to claim 50, wherein the said opening is located in the vicinity of the bottom of the bag and the total length of the obturator and the connecting means is less than the height of the bag from its bottom to the bottom of the hollow tube.

52. The combination according to claim 51, said connecting means comprising a flexible tube connected to the end of the obturator opposite from the distal end, said tube passing through said opening.

53. The combination according to claim 51, wherein the end of the obturator opposite the distal end engages the bag in the vicinity of said opening and connects with a flexible tube thereat which forms said connecting means.

* * * * *